(12) United States Patent
Li et al.

(10) Patent No.: US 11,581,489 B2
(45) Date of Patent: Feb. 14, 2023

(54) WHITE LIGHT EMITTING MATERIAL, PREPARATION METHOD THEREOF, AND APPLICATION THEREOF

(71) Applicant: SOUTH UNIVERSITY OF SCIENCE AND TECHNOLOGY OF CHINA, Shenzhen (CN)

(72) Inventors: Xiaomeng Li, Shenzhen (CN); Jieshun Cui, Shenzhen (CN); Xianglin Wang, Shenzhen (CN); Zhaoyu Zhang, Shenzhen (CN)

(73) Assignee: South University of Science and Technology of China, Shenzhen (CN)

( * ) Notice: Subject to any disclaimer, the term of this patent is extended or adjusted under 35 U.S.C. 154(b) by 305 days.

(21) Appl. No.: 16/945,060

(22) Filed: Jul. 31, 2020

(65) Prior Publication Data

US 2021/0036234 A1 Feb. 4, 2021

(30) Foreign Application Priority Data

Jul. 31, 2019 (CN) .......................... 201910700016.6

(51) Int. Cl.
*H01L 51/00* (2006.01)
*C07C 213/04* (2006.01)
(Continued)

(52) U.S. Cl.
CPC ........ *H01L 51/0059* (2013.01); *C07C 213/04* (2013.01); *C07C 217/80* (2013.01);
(Continued)

(58) Field of Classification Search
CPC .......................... H01L 51/0059; C07C 217/80
See application file for complete search history.

(56) References Cited

FOREIGN PATENT DOCUMENTS

| CN | 101805612 A | 8/2010 |
| CN | 106633089 A | 5/2017 |
| CN | 107245335 B | 8/2018 |

OTHER PUBLICATIONS

Niamnont et al, "Protein discrimination by fluorescent sensor array constituted of variously charged dendritic phenylene-ethynylene fluorophores," Biosensors and Bioelectronics 26 (2010), Aug. 1, 2010, pp. 863-867 (Year: 2010).*

(Continued)

*Primary Examiner* — Anthony Ho
(74) *Attorney, Agent, or Firm* — Jenkins, Wilson, Taylor & Hunt, PA

(57) ABSTRACT

A white light emitting material having a chemical structural formula represented by formula (I), a preparation method thereof and application thereof. The preparation method comprises subjecting tris(4-iodophenyl)amine and 4-methoxyphenylacetylene or tris(4-iodophenyl)amine and methyl 4-ethynylbenzoate to a coupling reaction under protection of a protective gas and catalysis of a Pd/Cu mixed catalyst, to obtain the white light emitting material. A novel temperature-sensitive light emitting material is synthesized through a one-step method. The material is applied to the field of diode luminescence based on the temperature-sensitive characteristic. White light luminescence can be finally realized only by reasonably controlling the temperature and duration time during heating a substrate. Compared with the existing art, the method greatly saves raw material costs and manufacturing process costs, and provides a novel idea and strategy for use of a white organic light emitting diode.

20 Claims, 4 Drawing Sheets

(51) Int. Cl.
      *C07C 217/80*     (2006.01)
      *C07C 227/26*     (2006.01)
      *C07C 229/52*     (2006.01)
      *C09K 11/06*      (2006.01)
      *H01L 51/50*      (2006.01)
      *H01L 51/52*      (2006.01)
      *H01L 51/56*      (2006.01)

(52) U.S. Cl.
     CPC .......... *C07C 227/26* (2013.01); *C07C 229/52* (2013.01); *C09K 11/06* (2013.01); *C09K 2211/1007* (2013.01); *C09K 2211/1014* (2013.01); *H01L 51/001* (2013.01); *H01L 51/5012* (2013.01); *H01L 51/5072* (2013.01); *H01L 51/5088* (2013.01); *H01L 51/5092* (2013.01); *H01L 51/5206* (2013.01); *H01L 51/56* (2013.01); *H01L 2251/558* (2013.01)

(56) References Cited

OTHER PUBLICATIONS

Niamnont et al, "A polyanionic dendritic fluorophore for selective detection of Hg2+ in triton X-100 aqueous media," Organic Letters, 2009, vol. 11, No. 13, pp. 2768-2771 (Year: 2009).*

* cited by examiner

WHITE LIGHT EMITTING MATERIAL, PREPARATION METHOD THEREOF, AND APPLICATION THEREOF

CROSS-REFERENCE OF RELATED APPLICATION

The present disclosure claims priority to Chinese Application No. CN201910700016.6 filed on Jul. 31, 2019 to the China National Intellectual Property Administration, the entire content of which is incorporated herein by reference.

TECHNICAL FIELD

The present disclosure belongs to the field of luminescence and display, and specifically relates to a white light emitting material, a preparation method thereof, and application thereof.

BACKGROUND

Because of advantages of high luminous efficiency, low energy consumption and long service life, white light emitting diodes have been applied to replace traditional incandescent lamps and daylight lamps, and mainly used in illumination and display. In recent years, there are many researches on white light emitting materials. For example, white light emitting materials with high energy efficiency have been synthesized by using rare earth coordination polymers. The rare earth coordination polymer is a kind of novel composite materials with various structures, strong adjustability and rich properties. For example, tungstate has been proved to be an important optical material due to its stable chemical properties and low phonon energy. For another example, vanadate is attracting more and more attention as an inorganic fluorescent material. It has good chemical stability and thermal stability, and is also a fluorescent synthetic material with high luminescence efficiency. Therefore, it has been widely applied.

CN106633089A discloses a white-light luminescent material comprising $Tb^{3+}/Eu^{3+}$ doped-rare earth coordination polymer and a preparation method thereof. The white-light luminescent material is synthesized by using 2,5-dihydroxyterephthalic acid as an organic ligand, using a simple solvent thermal synthesis method, and doping two rear earth metal ions in different proportions. The coordination compound prepared by this method can produce both the characteristic red light emission of the ion $Eu^{3+}$ and the blue light emission of the ligand at room temperature under the excitation of 370 nm ultraviolet. Thus, the relative strength of the red light emission and the blue light emission can be adjusted by adjusting the content of the ion $Eu^{3+}$ in the coordination compound, so that the coordination compound can emit white light. The preparation method is simple, and the raw materials can be easily obtained. The prepared coordination compound is useful as a novel white-light luminescent material.

CN107245335B discloses a tungstate-based white light-emitting material and a preparation method and application thereof. The tungstate-based white light-emitting material has a formula of $Ba_{0.05}Sr_{0.94-z}WO_4:0.01Tm^{3+}zDy^{3+}$, where z is 0.01-0.06. Under the excitation wavelength of 352-366 nm, the emitted light is in a white light region. Especially under the excitation wavelength of 354 nm, when z is 0.03, the light emitted by phosphor has color coordinates of (0.321, 0.347) and a color temperature of 6000K, which is the closest to standard white light. Therefore, the $Ba_{0.05}Sr_{0.94-z}WO_4:0.01Tm^{3+}zDy^{3+}$ provided by this invention is useful as a material for near-ultraviolet chip to excite white light.

CN101805612A discloses a method for preparing a white luminescent material comprising gallium-doped yttrium vanadate. The method includes the following steps: weighing gallium oxide and yttrium oxide according to a molar ratio of between 0.5 and 5 percent, and weighing vanadium pentoxide in an amount such that the molar ratio of the yttrium oxide to the vanadium pentoxide is in a range of between 76 and 99.6 percent; sufficiently mixing and grinding the weighed medicaments in an agate mortar; adding the mixed and ground medicaments in an alumina crucible; putting the alumina crucible into a muffle furnace with a controllable program for calcining at a heating speed of between 3 and 5° C./min; calcining the alumina crucible in atmosphere at the temperature of between 800 and 1,200° C.; keeping warm for 3 hours, and naturally cooling the alumina crucible to room temperature; taking the sample out of the alumina crucible; and grinding the sample to prepare the white luminescent material comprising gallium-doped yttrium vanadate. The luminescent material is prepared by adopting a high-temperature solid-phase method. The preparation method has the advantages of simple preparation method, less requirements for preparation condition, inexpensive raw materials, being readily for industrial production, and high product purity, and can be widely applied in the fields of LEDs, low-pressure mercury lamps and X-ray detectors.

However, the preparation methods of white light emitting materials in the existing art are relatively complicated, and various materials are often doped for use. What's more, the report about white light emitting materials in the existing art is limited. Therefore, it is meaningful to develop a new white light emitting material with simple preparation methods and low cost.

SUMMARY

To solve deficiencies in the existing art, an object of the present disclosure is to provide a novel white light emitting material, a preparation method thereof and application thereof.

To achieve the object, the present disclosure adopts the technical solutions described below.

In a first aspect, the present disclosure provides a white light emitting material having a chemical structural formula represented by formula (I).

Formula (I)

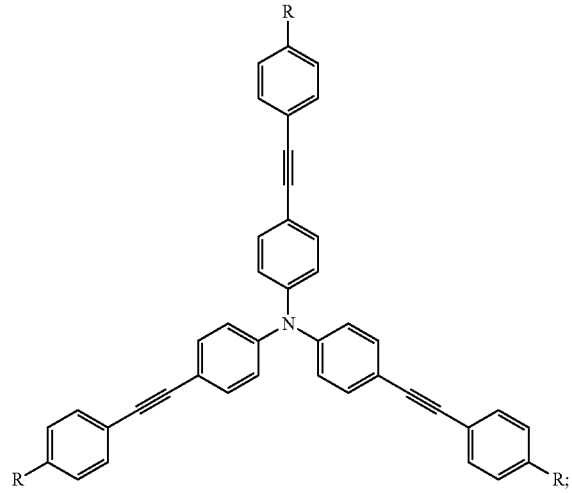

wherein —R is selected from —$OCH_3$ or —$COOCH_3$.

The white light emitting material provided by the present disclosure is a compound has the above-mentioned structure. This material is a new type of organic small molecular material with adjustable temperature dependent photoluminescence spectrum, and is useful in the field of diode luminescence. Light with different colors is emitted from different parts of the material upon nonuniform heating, and the light with different colors is mixed to produce white light. Therefore, it is only necessary to properly control the temperature and duration in the process of heating the substrate during preparation in order to finally realize white light luminescence. In the present disclosure, diodes are able to emit white light by using only a single organic light emitting material. Compared with the existing art, the method of the present disclosure greatly saves raw material costs and manufacturing process costs, and provides a novel idea and strategy for use of a white organic light emitting diode.

In a second aspect, the present disclosure provides a preparation method of the white light emitting material described above. The preparation method includes: subjecting tris(4-iodophenyl)amine and 4-methoxyphenylacetylene or tris(4-iodophenyl)amine and methyl 4-ethynylbenzoate to a coupling reaction under protection of a protective gas and catalysis of a Pd/Cu mixed catalyst, to obtain the white light emitting material.

Preferably, the protective gas is nitrogen.

Preferably, the Pd/Cu mixed catalyst is a catalyst consisting of tetrakis(triphenylphosphine)palladium and cuprous iodide.

Preferably, the molar ratio of tetrakis(triphenylphosphine) palladium to cuprous iodide is 1:(2 to 10), for example, 1:2, 1:1.5, 1:3, 1:4, 1:5, 1:6, 1:6.4, 1:7, 1:8, 1:9, 1:10, etc., preferably 1:6.4.

Preferably, the coupling reaction is carried out in a mixed solvent of tetrahydrofuran and trimethylamine.

Preferably, the volume ratio of tetrahydrofuran to triethylamine is (2 to 6):1, for example, 2:1, 2.5:1, 3:1, 3.5:1, 4:1, 30:7, 4.5:1, 5:1, 6:1, etc., preferably 30:7.

Preferably, the coupling reaction is carried out at 70° C. to 90° C., for example, 70° C., 72° C., 75° C., 78° C., 80° C., 82° C., 84° C., 85° C., 88° C., 90° C., etc., preferably 70° C.

Preferably, the product of the coupling reaction is purified by column chromatography.

In a third aspect, the present disclosure provides a white organic light emitting diode. The white organic light emitting diode includes a substrate, an anode layer, a hole injection layer, a white light emitting layer, an electron transport layer, an electron injection layer and a cathode layer, which are sequentially stacked; wherein a material for the white light emitting layer is the white light emitting material described above.

Preferably, a material for the anode layer includes indium tin oxide (ITO), fluorine-doped tin oxide (FTO), gold or graphene.

Preferably, a material for the hole injection layer includes polyethylenedioxythiophene-poly(styrenesulfonate), N,N'-dipheny-N,N'-(1-naphthyl)-1'1-biphenyl-4,4'-diamine (NPB), tirs(4-carbazole-9-yl-phenyl)amine (TCTA), or molybdenum trioxide.

Preferably, a material for the electron transport layer includes 1,3,5-tris(1-phenyl-1H-benzimidazol-2-yl)benzene (TPBi), bathophenanthroline (Bphen) or 1,3-bis(3,5-di(pyridin-3-yl)phenyl)benzene (B3PyPB).

Preferably, a material for the electron injection layer comprises lithium fluoride, cesium fluoride, or 8-hydroxyquinolinolato lithium.

Preferably, a material for the cathode layer includes aluminum, silver, magnesium silver alloy, or calcium.

Preferably, the mass ratio of magnesium to silver in the magnesium silver alloy is 1:(8 to 12), for example, 1:8, 1:9, 1:10, 1:11, 1:12, etc.

Preferably, the substrate includes a glass film, a quartz film, a polyimide film, a polyethylene terephthalate film, or a metal film.

Preferably, the anode layer has a thickness of 100 nm to 300 nm, for example, 100 nm, 120 nm, 150 nm, 180 nm, 200 nm, 220 nm, 250 nm, 300 nm, etc.

Preferably, the hole injection layer has a thickness of 10 nm to 30 nm, for example, 10 nm, 12 nm, 15 nm, 18 nm, 20 nm, 22 nm, 25 nm, 28 nm, 30 nm, etc.

Preferably, the white light emitting layer has a thickness of 20 nm to 60 nm, for example, 20 nm, 25 nm, 30 nm, 35 nm, 40 nm, 45 nm, 50 nm, 55 nm, 60 nm, etc.

The thickness of the white light emitting layer is specifically selected from the range of 20 nm to 60 nm. This is because if the thickness exceeds 60 nm, the device will have a high resistance, and generate excessive heat during working, which will affect the color of the emitted light; and if the thickness is less than 20 nm, the light emitting materials get reduced, which will lower the luminescence efficiency.

Preferably, the electron transport layer has a thickness of 20 nm to 60 nm, for example, 20 nm, 25 nm, 30 nm, 35 nm, 40 nm, 45 nm, 50 nm, 55 nm, 60 nm, etc.

Preferably, the electron injection layer has a thickness of 0.2 nm to 0.8 nm, for example, 0.2 nm, 0.25 nm, 0.3 nm, 0.35 nm, 0.4 nm, 0.5 nm, 0.6 nm, 0.7 nm, 0.8 nm, etc.

Preferably, the cathode layer has a thickness of 80 nm to 200 nm, for example, 80 nm, 90 nm, 100 nm, 110 nm, 120 nm, 140 nm, 150 nm, 180 nm, 200 nm, etc.

In a fourth aspect, the present disclosure provides a preparation method of the white organic light emitting diode described above. The preparation method includes: taking a substrate material with an anode layer, and sequentially preparing and forming a hole injection layer, a white light emitting layer, an electron transport layer, an electron injection layer and a cathode layer on the anode layer sequentially, to obtain the white organic light emitting diode.

Preferably, a manner of preparation and formation comprises any one or a combination of at least two of thermal evaporation, spin coating, brush coating, spray coating, roll coating, printing or ink jet printing.

Preferably, the preparation method includes the following steps:

(1) taking a substrate material with an anode layer, and spin-coating a hole injection layer material on a surface of the anode layer to form a hole injection layer;

(2) heating the product obtained in the step (1);

(3) depositing a white light emitting material on the hole injection layer of the product obtained in the step (2) via thermal vacuum evaporation to form a white light emitting layer;

(4) heating the product obtained in the step (3), and cooling the product; and (5) depositing an electron transport layer, an electron injection layer and a cathode layer on the white light emitting layer of the product obtained in the step (4) sequentially, to obtain the white organic light emitting diode.

Preferably, before the hole injection layer material is spin-coated on the surface of the anode layer material in the step (1), the substrate material with an anode layer is ultrasonically washed in purified water, acetone and isopropanol sequentially for 5 min to 20 min respectively, for example, 5 min, 8 min, 10 min, 12 min, 15 min, 18 min, 20 min, etc.

Preferably, the heating in the step (2) refers to heating the product obtained in the step (1) to a temperature between 130° C. and 170° C. (for example, 130° C., 135° C., 140° C., 145° C., 150° C., 160° C., 170° C., etc.) and keeping at this temperature for 10 min to 20 min (for example, 10 min, 12 min, 14 min, 15 min, 16 min, 18 min, 20 min).

Preferably, the thermal vacuum evaporation in the step (3) is carried out under an atmospheric pressure of $10^{-5}$ to $10^{-4}$ Pa, for example, $10^{-5}$ Pa, $2\times10^{-5}$ Pa, $4\times10^{-5}$ Pa, $6\times10^{-5}$ Pa, $8\times10^{-5}$ Pa, $10^{-4}$ Pa, etc.

Preferably, a rate of the thermal vacuum evaporation in the step (3) is 0.1 Å/sec to 0.5 Å/sec, for example, 0.1 Å/sec, 0.2 Å/sec, 0.3 Å/sec, 0.4 Å/sec, 0.5 Å/sec, etc.

Preferably, the heating in the step (4) refers to heating to a temperature between 120° C. and 230° C. (for example, 120° C., 150° C., 160° C., 180° C., 200° C., 210° C., 220° C., 230° C., etc.) within 10 seconds and keeping at this temperature for 10 s to 1 min (for example, 10 s, 20 s, 30 s, 40 s, 50 s, 1 min, etc.).

The heating is carried out by heating the substrate of product. The heating temperature and time are controlled under the conditions described above to enable the product to emit white light. If the temperature is lower than 120° C. or the duration time is shorter than 10 s, the product finally emits blue light; if the temperature exceeds 230° C. or the duration exceeds 1 min, the product emits red light.

Preferably, the cooling in the step (4) refers to cooling to a temperature between 20° C. and 30° C. within 3 min (for example, 20° C., 22° C., 24° C., 25° C., 26° C., 27° C., 28° C., 29° C., 30° C., etc.).

Only when the above-mentioned cooling conditions are satisfied can the luminous color emitted by the light emitting material after heated be within the white light range.

As a preferable technical solution of the present disclosure, the preparation method includes the following steps:

(1) ultrasonically washing a substrate material with an anode layer in purified water, acetone and isopropanol sequentially for 5 min to 20 min respectively;

(2) spin-coating a hole injection layer material on a surface of the anode layer cleaned in the step (1) to form a hole injection layer;

(3) heating the product obtained in the step (2) to a temperature between 130° C. and 170° C., and keeping at this temperature for 10 min to 20 min;

(4) depositing a white light emitting material on the hole injection layer of the product obtained in the step (3) via thermal vacuum evaporation at a rate of 0.1 Å/sec to 0.5 Å/sec under an atmospheric pressure of $10^{-5}$ Pa to $10^{-4}$ Pa to form a white light emitting layer;

(5) heating the product obtained in the step (4) to a temperature between 120° C. and 230° C. within 10 s, then keeping at this temperature for 10 s to 1 min, and cooling to a temperature between 20° C. and 30° C. within 3 min; and (6) depositing an electron transport layer, an electron injection layer and a cathode layer on the white light emitting layer of the product obtained in the step (5) sequentially, to obtain the white organic light-emitting diode.

Compared with the existing art, the present disclosure has beneficial effects described below.

The present disclosure synthesizes a novel temperature-sensitive light emitting material through a one-step method. The material is applied to the field of diode luminescence based on the temperature-sensitive characteristic. Light with different colors is emitted from different parts of the material upon nonuniform heating, and the light with different colors is mixed to produce white light. Therefore, it is only necessary to properly control the temperature and duration in the process of heating the substrate during preparation in order to finally realize white light luminescence. The present disclosure can realize white light luminescence of diodes only by using a single organic light emitting material. Compared with the existing art, the method greatly saves raw material costs and manufacturing process costs, and provides a novel idea and strategy for use of a white organic light emitting diode.

DETAILED DESCRIPTION

The technical solutions of the present disclosure are further described below through specific examples. Those skilled in the art should understand that the examples described herein are merely used for a better understanding of the present disclosure and should not be construed as specific limitations to the present disclosure.

Example 1

A white light emitting material having a chemical structural formula represented by the following formula is synthesized in this example.

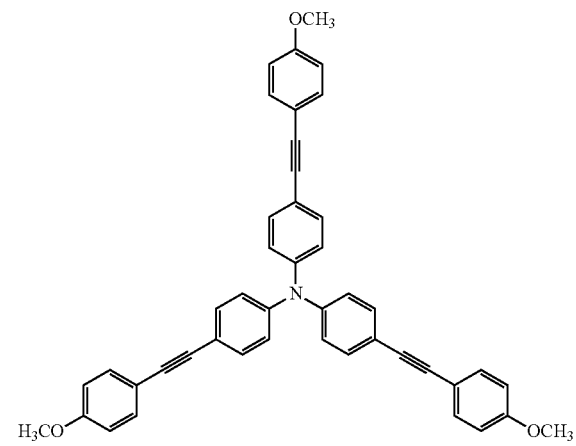 [SMILES: COc1ccc(C#Cc2ccc(N(c3ccc(C#Cc4ccc(OC)cc4)cc3)c3ccc(C#Cc4ccc(OC)cc4)cc3)cc2)cc1]

The preparation method includes steps described below.

(1) 5.0 mmol of tris(4-iodophenyl)amine, 21.0 mmol of 4-methoxyphenylacetylene, 30.0 mL of tetrahydrofuran and 7.0 mL of trimethylamine were loaded into a 100 mL two-necked flask equipped with a stir bar and connected to a reflux tube.

(2) The reaction mixture was vacuumized by using a vacuum pump. The pressure reached $1\times10^{-2}$ Pa before nitrogen was introduced. Vacuuming and refilling nitrogen were repeatedly carried out for three times, and the reaction system was kept under an atmosphere of nitrogen.

(3) 0.125 mmol of tetrakis(triphenylphosphine)palladium and 0.8 mmol of cuprous iodide were added into the reaction solution under an atmosphere of nitrogen.

(4) The reaction mixture was heated to 70° C. under the protection of nitrogen and kept refluxing for 10 hours. The solvent was then evaporated by using a rotary evaporator, and the residue was washed with a small amount of ethyl acetate to give yellow powder, which was purified by column chromatography (silica column: Yantai Jiangyou F-254 200-300 mesh, mobile phase: a mixed solvent of dichloromethane and n-hexane in a volume ratio of 1:30) to obtain white solid powder, i.e., the white light emitting material.

Figure 1:
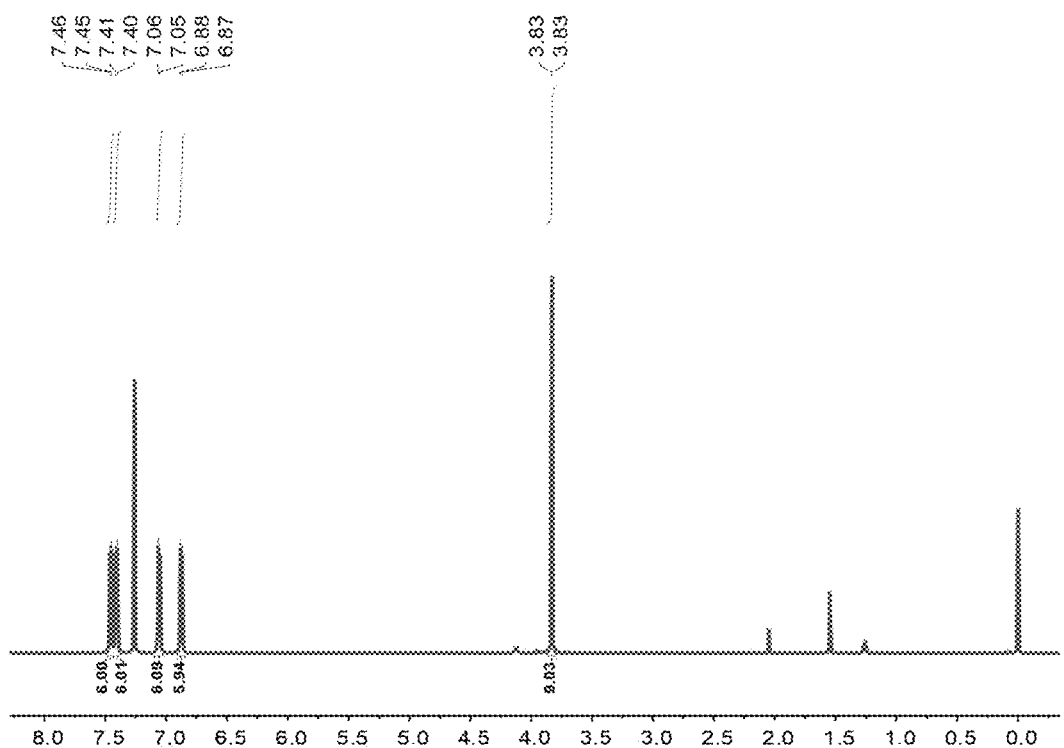
FIG. 1 is a $^1$hydrogen-nuclear magnetic resonance ($^1$H-NMR) characteristic diagram of a compound in Example 1.

The obtained white solid powder was characterized by C nuclear magnetic resonance ($^{13}$C NMR) and $^1$H NMR. The $^1$H NMR data is shown in FIG. 1, and specifically is: $^1$H NMR (Bruker 600 MHz, CDCl$_3$) δ 7.45 (doublet, J=7.1 Hz, 6H), 7.43-7.38 (multiplet, 6H), 7.09-7.02 (multiplet, 6H), 6.91-6.85 (multiplet, 6H), 3.83 (singlet, 9H).

Figure 2:
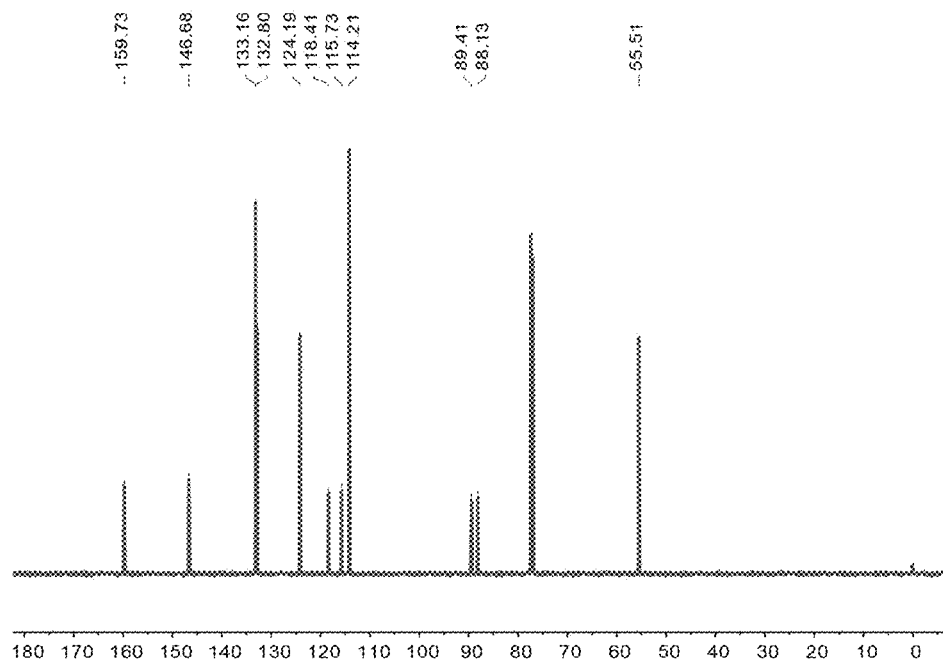
FIG. 2 is a $^1$H-NMR characteristic diagram of the compound in Example 1.

The $^{13}$C NMR data is shown in FIG. 2, and specifically is: $^{13}$C NMR (Bruker 151 MHz, CDCl$_3$) chemical shift δ 159.73, 146.68, 133.16, 132.80, 124.19, 118.41, 115.73, 114.21, 89.41, 88.13, 55.51.

The data proves that this compound was successfully synthesized.

Example 2

A white light emitting material having a chemical structural formula represented by the following formula is synthesized in this example.

The preparation method includes steps described below.

(1) 5.0 mmol of tris(4-iodophenyl)amine, 21.0 mmol of methyl 4-ethynylbenzoate, 30.0 mL of tetrahydrofuran and 7.0 mL of trimethylamine were loaded into a 100 mL two-necked flask equipped with a stir bar and connected to a reflux tube.

(2) The reaction mixture was vacuumed by a vacuum pump. The pressure reached $1\times10^{-2}$ Pa before nitrogen was introduced. Vacuuming and refilling nitrogen were repeatedly carried out for three times, and the reaction system was kept under an atmosphere of nitrogen.

(3) 0.125 mmol of tetrakis(triphenylphosphine)palladium and 0.8 mmol of cuprous iodide were added into the reaction solution under an atmosphere of nitrogen.

(4) The reaction mixture was heated to 70° C. under the protection of nitrogen and kept refluxing for 10 hours. The solvent was then evaporated by using a rotary evaporator, and the residue was washed with a small amount of ethyl acetate to give yellow powder, which was purified by column chromatography (silica column: Yantai Jiangyou F-254 200-300 mesh, mobile phase: a mixed solvent of dichloromethane and n-hexane in a volume ratio of 1:30) to obtain white solid powder, i.e., the white light emitting material.

Figure 3:
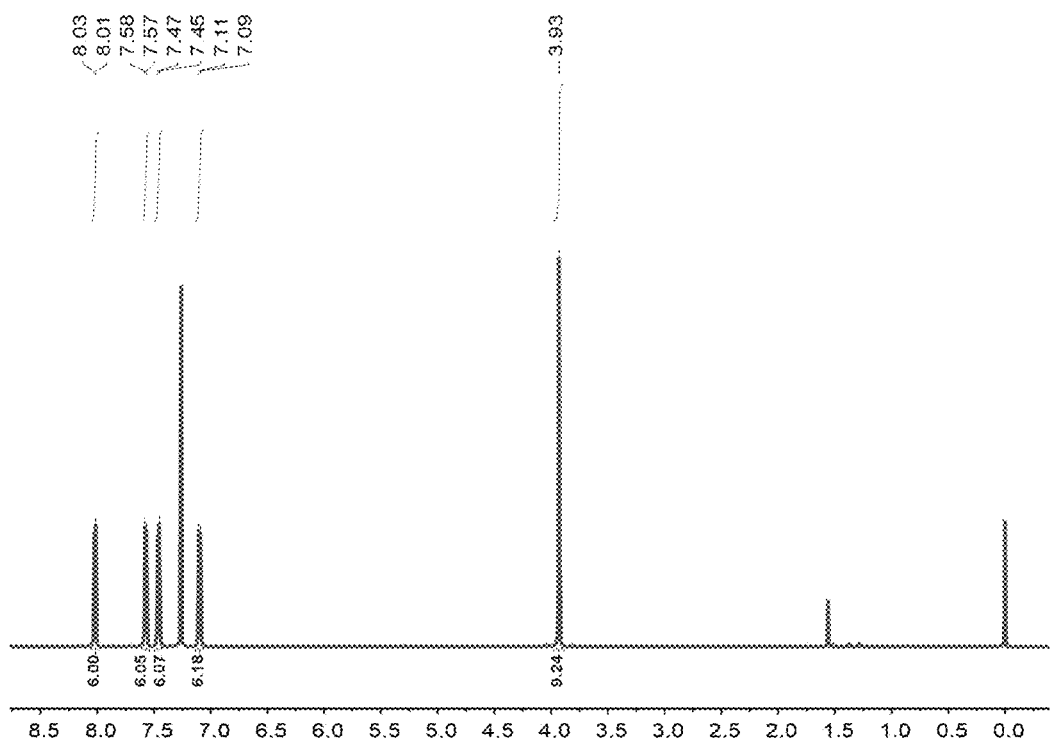
FIG. 3 is a $^1$H-NMR characteristic diagram of a compound in Example 2.

The obtained white solid powder was characterized by $^1$H NMR and $^{13}$C NMR. The $^1$H NMR data is shown in FIG. 3, and specifically is: $^1$H NMR (Bruker 600 MHz, CDCl$_3$) chemical shift δ 8.02 (doublet, J=8.3 Hz, 6H), 7.57 (doublet, J=8.4 Hz, 6H), 7.46 (doublet, J=8.6 Hz, 6H), 7.10 (doublet, J=8.7 Hz, 6H), 3.93 (singlet, 9H).

Figure 4:
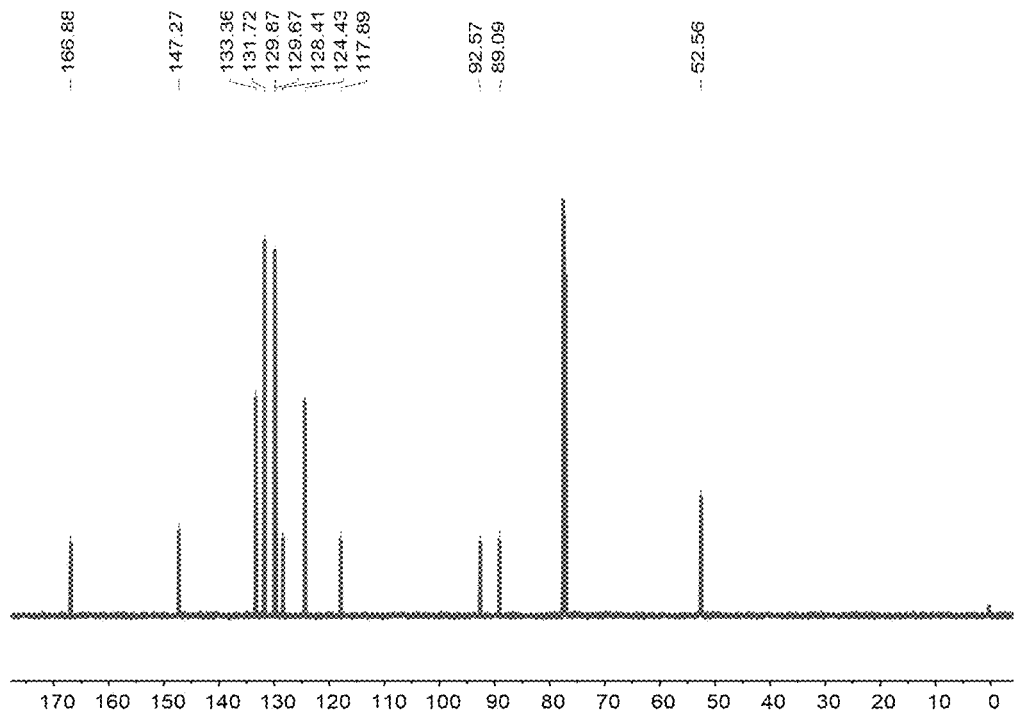
FIG. 4 is a $^1$H-NMR characteristic diagram of the compound in the example 2.

The $^{13}$C NMR data is shown in FIG. 4, and specifically is: $^{13}$C NMR (Bruker 151 MHz, CDCl$_3$) chemical shift δ 166.57, 146.96, 133.05, 131.40, 129.55, 129.36, 128.09, 124.11, 117.58, 92.26, 88.77, 52.24.

The data proves that this compound was successfully synthesized.

Example 3

A white organic light emitting diode is provided in this example. The preparation method of the white organic light emitting diode includes steps described below.

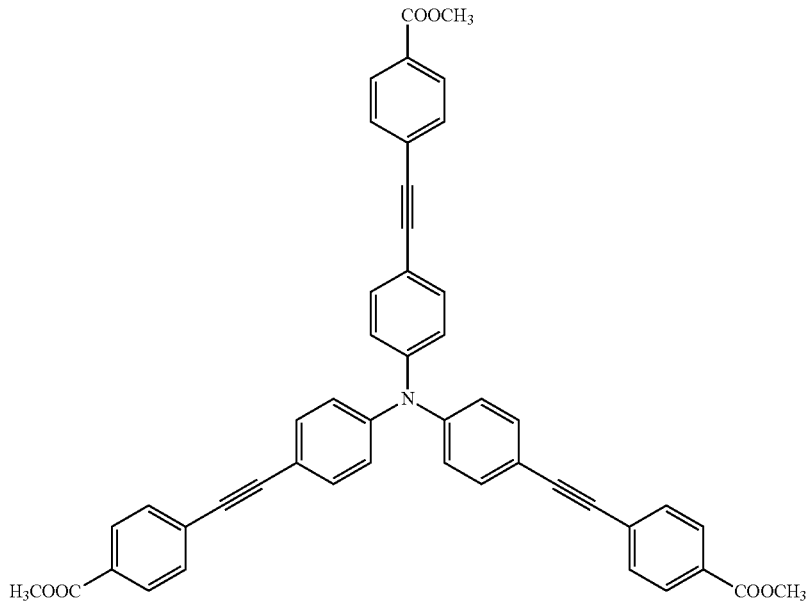

(1) A glass substrate with 200 nm ITO as the anode material was ultrasonically washed for 15 min in purified water, acetone and isopropanol sequentially.

(2) 20 nm-thick polyethylenedioxythiophene-poly(styrenesulfonate) was spin-coated on the surface of the ITO material cleaned in the step (1).

(3) The product obtained in the step (2) was placed on a heating table, and heated to 150° C., and then kept at this temperature for 15 min.

(4) The material prepared in the example 1 was deposited on the polyethylenedioxythiophene-poly(styrenesulfonate) layer of the product obtained in the step (3) via thermal vacuum evaporation at a rate of 0.5 Å/sec at an atmospheric pressure of $10^{-5}$ Pa to form a 40 nm white light emitting layer.

(5) The product obtained in the step (4) was heated to 150° C. within 10 s, kept for 20 s, and then cooled to 25° C. within 3 min.

(6) A 40 nm TPBi layer, a 0.5 nm lithium fluoride layer and a 130 nm aluminum layer were sequentially deposited on the white light emitting layer of the product obtained in the step (5) to obtain the white organic light emitting diode.

Example 4

A white organic light emitting diode is provided in this example. The preparation method of the white organic light emitting diode includes steps described below.

(1) A glass substrate with 100 nm ITO as the anode material was ultrasonically washed for 20 min in purified water, acetone and isopropanol sequentially.

(2) 30 nm-thick polyethylenedioxythiophene-poly(styrenesulfonate) was spin-coated on the surface of the ITO material cleaned in the step (1).

(3) The product obtained in the step (2) was placed on a heating table, and heated to 130° C., and then kept at this temperature for 20 min.

(4) The material prepared in Example 2 was deposited on the polyethylenedioxythiophene-poly(styrenesulfonate) layer of the product obtained in the step (3) via thermal vacuum evaporation at a rate of 0.3 Å/sec at an atmospheric pressure of $10^{-5}$ Pa to form a 60 nm white light emitting layer.

(5) The product obtained in the step (4) was heated to 200° C. within 10 s, kept for 10 s, and then cooled to 25° C. within 3 min.

(6) A 20 nm TPBi layer, a 0.8 nm lithium fluoride layer and an 80 nm aluminum layer were sequentially deposited on the white light emitting layer of the product obtained in the step (5) to obtain the white organic light emitting diode.

Example 5

A white organic light emitting diode is provided in this example. The preparation method of the white organic light emitting diode includes steps described below.

(1) A glass substrate with 300 nm ITO as the anode material was ultrasonically washed for 15 min in purified water, acetone and isopropanol sequentially.

(2) 10 nm-thick polyethylenedioxythiophene-poly(styrenesulfonate) was spin-coated on the surface of the ITO material cleaned in the step (1).

(3) The product obtained in the step (2) was placed on a heating table, and heated to 170° C., and then kept at this temperature for 10 min.

(4) The material prepared in Example 1 was deposited on the polyethylenedioxythiophene-poly(styrenesulfonate) layer of the product obtained in the step (3) via thermal vacuum evaporation at a rate of 0.5 Å/sec at an atmospheric pressure of $10^{-4}$ Pa to form a 20 nm white light emitting layer.

(5) The product obtained in the step (4) was heated to 170° C. within 10 s, kept for 30 s, and then cooled to 25° C. within 3 min.

(6) A 60 nm TPBi layer, a 0.2 nm lithium fluoride layer and a 200 nm aluminum layer were sequentially deposited on the white light emitting layer of the product obtained in the step (5) to obtain the white organic light emitting diode.

Example 6

A white organic light emitting diode is provided in this example. The preparation method of the white organic light emitting diode includes steps described below.

(1) A glass substrate with 200 nm graphene as the anode material was ultrasonically washed for 15 min in purified water, acetone and isopropanol sequenctially.

(2) 20 nm-thick molybdenum trioxide was spin-coated on the surface of the graphene material cleaned in the step (1).

(3) The product obtained in the step (2) was placed on a heating table, and heated to 150° C., and then kept at this temperature for 15 min.

(4) The material prepared in Example 1 was deposited on the molybdenum trioxide layer of the product obtained in the step (3) via thermal vacuum evaporation at a rate of 0.5 Å/sec at an atmospheric pressure of $10^{-5}$ Pa to form a 40 nm white light emitting layer.

(5) The product obtained in the step (4) was heated to 120° C. within 10 s, kept for 1 min, and then cooled to 20° C. within 3 min.

(6) A 40 nm bathophenanthroline layer, a 0.5 nm cesium fluoride layer and a 130 nm magnesium silver alloy layer were sequentially deposited on the white light emitting layer of the product obtained in the step (5) to obtain the white organic light emitting diode.

Example 7

A white organic light emitting diode is provided in this example. The preparation method of the white organic light emitting diode includes steps described below.

(1) A glass substrate with 200 nm gold as the anode material was ultrasonically washed for 15 min in purified water, acetone and isopropanol sequentially.

(2) 20 nm-thick TCTA was spin-coated on the surface of the gold material cleaned in the step (1).

(3) The product obtained in the step (2) was placed on a heating table, and heated to 150° C., and then kept at this temperature for 15 min.

(4) The material prepared in Example 2 was deposited on the TCTA layer of the product obtained in the step (3) via thermal vacuum evaporation at a rate of 0.5 Å/sec at an atmospheric pressure of $10^{-5}$ Pa to form a 40 nm white light emitting layer.

(5) The product obtained in the step (4) was heated to 230° C. within 10 s, kept for 10 s, and then cooled to 30° C. within 3 min.

(6) A 40 nm B3PyPB layer, a 0.5 nm 8-hydroxyquinolinato lithium layer and a 130 nm sliver layer were sequentially deposited on the white light emitting layer of the product obtained in the step (5) to obtain the white organic light emitting diode.

Example 8

Evaluation:

The performance of the white organic light emitting diodes prepared in the example 3 and example 4 were evaluated as follows.

(1) Luminance-current density-voltage curve test: A Keithley Model 2634 type source meter was connected to the anode end and the cathode end of the organic light emitting diode. The voltage between the anode and the cathode was adjusted for scanning, where the scanning area was 0 V to 15 V, and the current value and the voltage value were recorded. The corresponding luminance value was read out by a PR670 luminance meter, and a luminance-current density-voltage curve was drawn.

Figure 5:
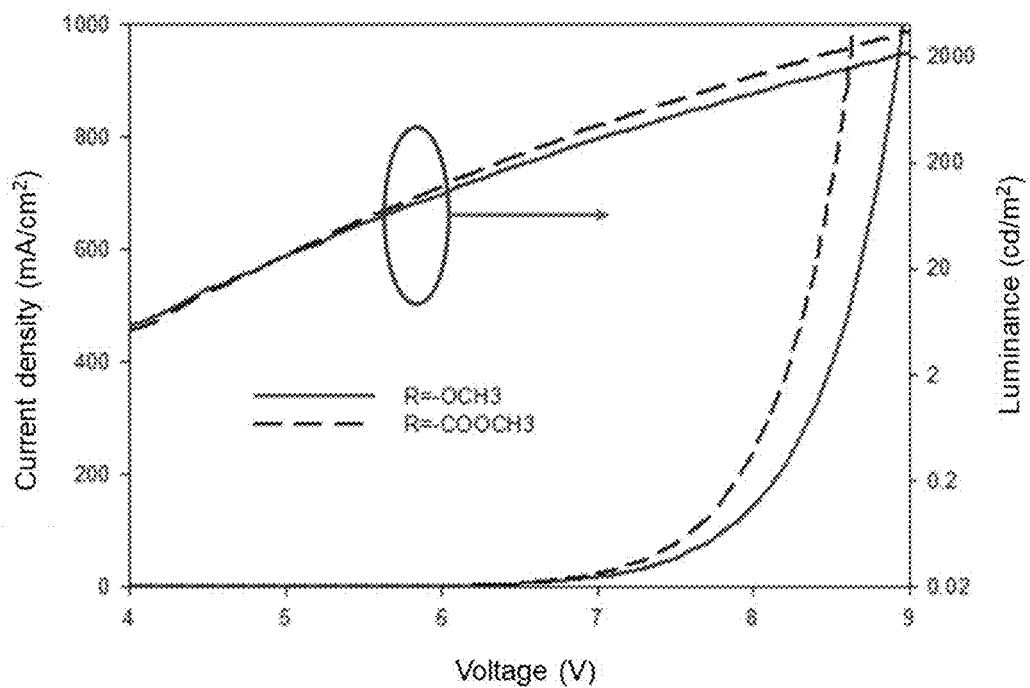
FIG. 5 is a luminance-current density-voltage curve graph of a white organic light emitting diode.

The test results are shown in FIG. 5 (the arrow in the figure indicates that the vertical coordinate of the circled curves is the luminance on the right-hand side). It can be seen from the graph that: the turn-on voltage of the light emitting diode is about 6 V, and the maximum luminance is about 2000 cd/m².

(2) Emission spectrum-current density curve test: A Keithley Model 2634 type source meter was connected to the anode end and the cathode end of the organic light emitting diode. The mode was adjusted to be a current source mode, and the current density value was adjusted to be from 1 mA/cm$_2$ to 50 mA/cm$_2$. The spectrum of the light emitting diode was tested by using an ocean spectrometer 2000.

Figure 6:
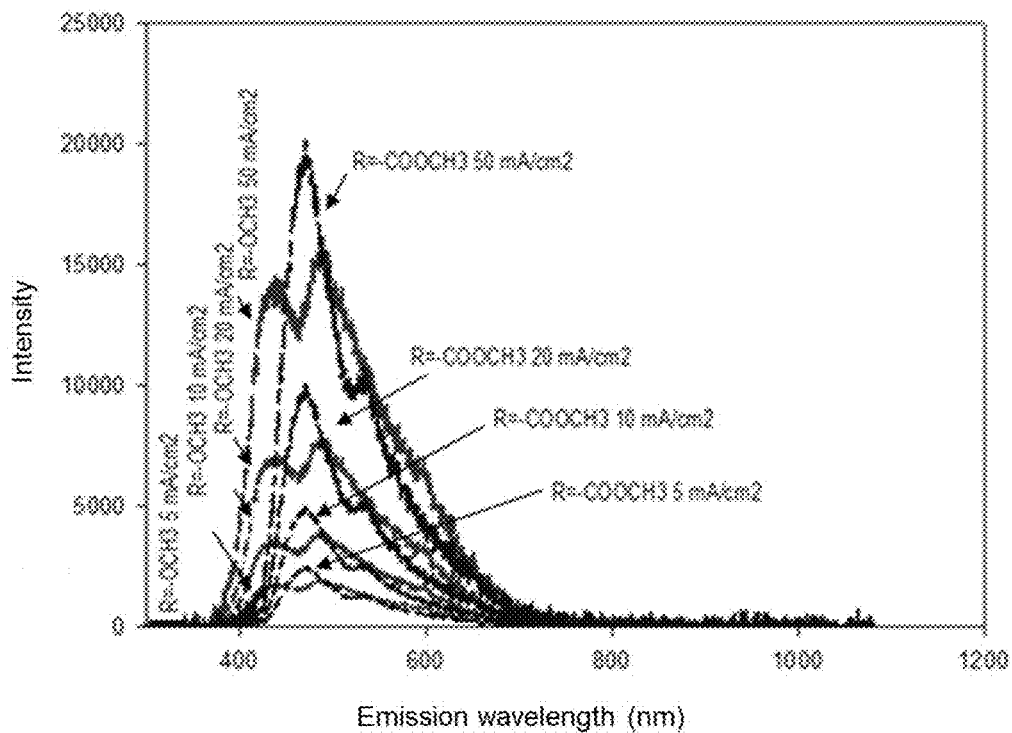
FIG. 6 is an emission spectrum-current density curve graph of a white organic light emitting diode.

The test results are shown in FIG. 6, and it can be seen from the graph that the peak value of the light emitting spectrum has no large shift under different current densities, suggesting that the light emitting diode has excellent color stability.

(3) Color coordinate test: A Keithley Model 2634 source meter was connected to the anode end and the cathode end of the organic light emitting diode. The mode was adjusted to be a current source mode, and the current density value was adjusted to be 10 mA/cm$_2$. The spectrum of the light emitting diode was tested by using an ocean spectrometer 2000, and the color coordinate was measured by using spectrasite software.

Figure 7:
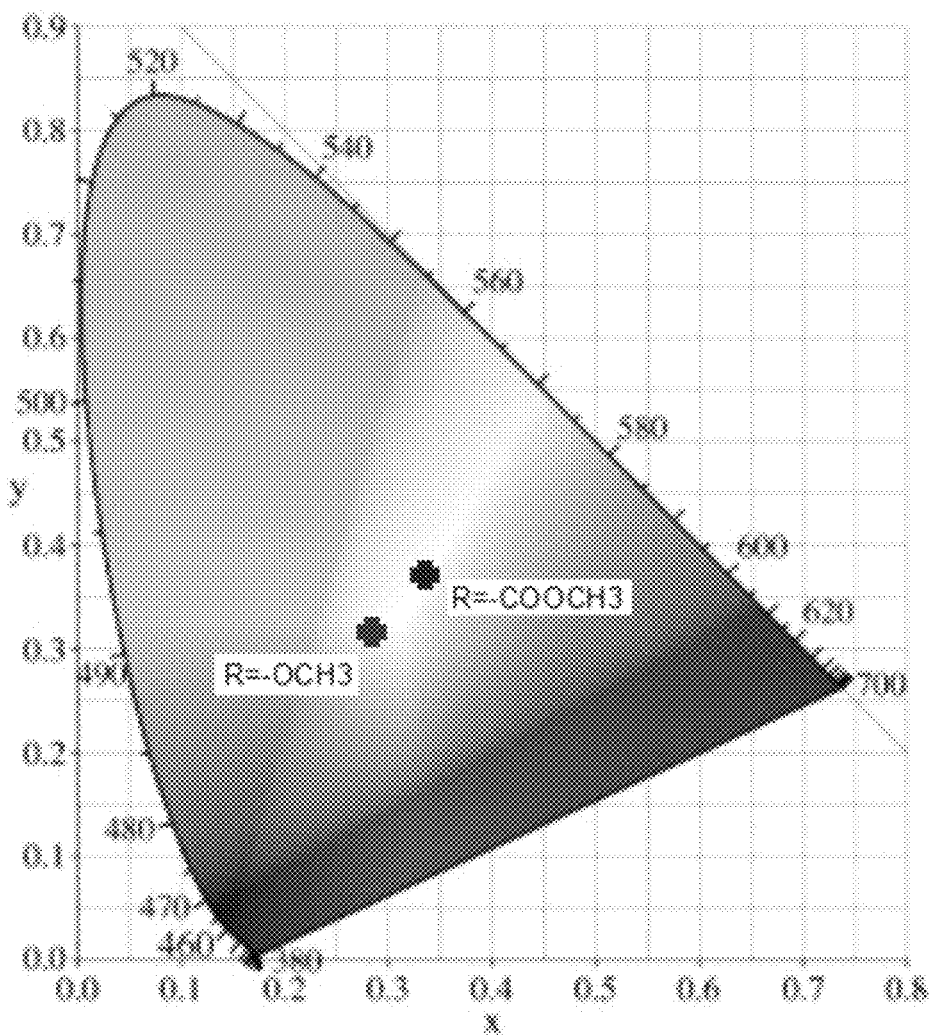
FIG. 7 is a color coordinate diagram of a white organic light emitting diode.

The test results are shown in FIG. 7, and it can be seen from the graph that, when the substituent —R is —OCH$_3$, the color coordinates of the light emitting diode are (0.2938, 0.3104), and when the substituent —R is —COOCH$_3$, the color coordinates of the light emitting diode are (0.3483, 0.3509).

The applicant has stated that although the white light emitting material, a preparation method thereof, and application thereof in the present disclosure are described through the examples described above, the present disclosure is not limited to the examples described above, which means that implementation of the present disclosure does not necessarily depend on the examples described above. It should be apparent to those skilled in the art that any improvements made to the present disclosure, equivalent replacements of various raw materials of the product, the addition of adjuvant ingredients, and the selection of specific manners, etc. in the present disclosure all fall within the protection scope and the scope of disclosure of the present disclosure.

Though the preferred embodiments of the present disclosure have been described above in detail, the present disclosure is not limited to the above-described embodiments, and various simple modifications can be made to the technical solutions of the present disclosure without departing from the scope of the present disclosure. These simple modifications are all within the scope of the present disclosure.

In addition, it is to be noted that if not in collision, the specific technical features described in the above specific embodiments may be combined in any suitable manner. In order to avoid unnecessary repetition, the present disclosure does not further specify any of various possible combination manners.

The invention claimed is:

1. A white light emitting material having a chemical structural formula represented by formula (I):

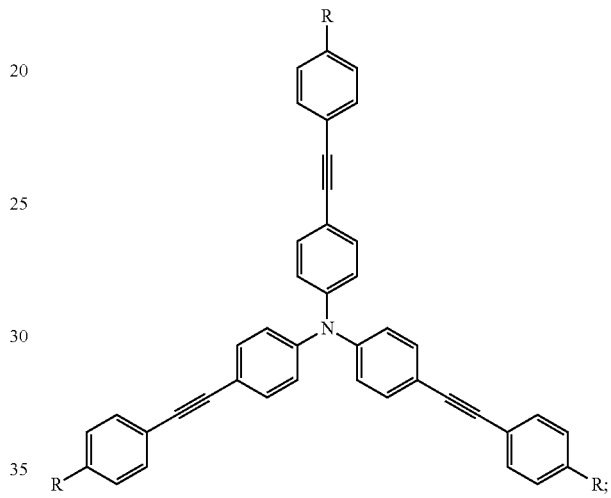

Formula (I)

wherein —R is selected from —OCH$_3$ or —COOCH$_3$.

2. A preparation method of the white light emitting material of claim 1, comprising: subjecting tris(4-iodophenyl)amine and 4-methoxyphenylacetylene or tris(4-iodophenyl)amine and methyl 4-ethynylbenzoate to a coupling reaction under protection of a protective gas and catalysis of a Pd/Cu mixed catalyst, to obtain the white light emitting material.

3. The preparation method of the white light emitting material of claim 2, wherein the protective gas is nitrogen.

4. The preparation method of the white light emitting material of claim 2, wherein the Pd/Cu mixed catalyst is a catalyst consisting of tetrakis(triphenylphosphine)palladium and cuprous iodide;

optionally, a molar ratio of tetrakis(triphenylphosphine)palladium to cuprous iodide is 1:(2 to 10).

5. The preparation method of the white light emitting material of claim 2, wherein the coupling reaction is carried out in a mixed solvent of tetrahydrofuran and triethylamine;

optionally, a volume ratio of tetrahydrofuran to triethylamine is (2 to 6):1.

6. The preparation method of the white light emitting material of claim 2, wherein the coupling reaction is carried out at 70° C. to 90° C.;

optionally, a product of the coupling reaction is purified by column chromatography.

7. A white organic light emitting diode, comprising a substrate, an anode layer, a hole injection layer, a white light emitting layer, an electron transport layer, an electron injection layer and a cathode layer, which are sequentially stacked, wherein a material for the white light emitting layer is the white light emitting material of claim 1.

8. The white organic light emitting diode of claim 7, wherein a material for the anode layer comprises indium tin oxide, fluorine-doped tin oxide, gold or graphene.

9. The white organic light emitting diode of claim 7, wherein a material for the hole injection layer comprises polyethylenedioxythiophene-poly(styrenesulfonate), N,N'-dipheny-N,N'-(1-naphthyl)-1'1-biphenyl-4,4'-diamine, tirs (4-carbazole-yl-phenyl)amine, or molybdenum trioxide.

10. The white organic light emitting diode of claim 7, wherein a material for the electron transport layer comprises 1,3,5-tris(1-phenyl-1H-benzimidazol-2-yl)benzene, bathophenanthroline or 1,3-bis(3,5-di(pyridin-3-yl)phenyl)benzene.

11. The white organic light emitting diode of claim 7, wherein a material for the electron injection layer comprises lithium fluoride, cesium fluoride, or 8-hydroxyquinolinolato lithium.

12. The white organic light emitting diode of claim 7, wherein a material for the cathode layer comprises aluminum, silver, magnesium silver alloy, or calcium;
optionally, a mass ratio of magnesium to silver in the magnesium silver alloy is 1:(8 to 12).

13. The white organic light emitting diode of claim 7, wherein, the substrate comprises a glass film, a quartz film, a polyimide film, a polyethylene terephthalate film, or a metal film.

14. The white organic light emitting diode of claim 7, wherein the anode layer has a thickness of 100 nm to 300 nm;
optionally, the hole injection layer has a thickness of 10 nm to 30 nm;
optionally, the white light emitting layer has a thickness of 20 nm to 60 nm;
optionally, the electron transport layer has a thickness of 20 nm to 60 nm;
optionally, the electron injection layer has a thickness of 0.2 nm to 0.8 nm;
optionally, the cathode layer has a thickness of 80 nm to 200 nm.

15. A preparation method of the white organic light emitting diode of claim 7, comprising: taking a substrate material with an anode layer, and sequentially preparing and forming a hole injection layer, a white light emitting layer, an electron transport layer, an electron injection layer and a cathode layer on the anode layer sequentially, to obtain the white organic light emitting diode.

16. The preparation method of the white organic light emitting diode of claim 15, wherein a manner of preparation and formation comprises any one or a combination of at least two of thermal evaporation, spin coating, brush coating, spray coating, roll coating, printing or ink jet printing.

17. The preparation method of the white organic light emitting diode of claim 16, wherein the preparation method comprises the following steps:
(1) taking a substrate material with an anode layer, and spin-coating a hole injection layer material on a surface of the anode layer to form a hole injection layer;
(2) heating the product obtained in the step (1);
(3) depositing a white light emitting material on the hole injection layer of the product obtained in the step (2) via thermal vacuum evaporation to form a white light emitting layer;
(4) heating the product obtained in the step (3), and cooling the product; and
(5) depositing an electron transport layer, an electron injection layer and a cathode layer on the white light emitting layer of the product obtained in the step (4) sequentially, to obtain the white organic light emitting diode.

18. The preparation method of the white organic light emitting diode of claim 17, further comprising: ultrasonically washing the substrate material with an anode layer in purified water, acetone and isopropanol sequentially for 5 min to 20 min respectively, before the hole injection layer material is spin-coated on the surface of the anode layer material in the step (1).

19. The preparation method of the white organic light emitting diode of claim 17, wherein the heating in the step (2) refers to heating the product obtained in the step (1) to a temperature between 130° C. and 170° C. and keeping at this temperature for 10 min to 20 min;
optionally, the thermal vacuum evaporation in the step (3) is carried out under an atmospheric pressure of $10^{-5}$ to $10^{-4}$ Pa;
optionally, a rate of the thermal vacuum evaporation in the step (3) is 0.1 Å/sec to 0.5 Å/sec;
optionally, the heating in the step (4) refers to heating to a temperature between 120° C. and 230° C. within 10 s and keeping at this temperature for 10 s to 1 min;
optionally, the cooling in the step (4) refers to cooling to a temperature between 20° C. and 30° C. within 3 min.

20. The preparation method of the white organic light emitting diode of claim 17, wherein the preparation method comprises the following steps:
(1) ultrasonically washing a substrate material with an anode layer in purified water, acetone and isopropanol sequentially for 5 min to 20 min respectively;
(2) spin-coating a hole injection layer material on a surface of the anode layer cleaned in the step (1) to form a hole injection layer;
(3) heating the product obtained in the step (2) to a temperature between 130° C. and 170° C., and keeping at this temperature for 10 min to 20 min;
(4) depositing a white light emitting material on the hole injection layer of the product obtained in the step (3) via thermal vacuum evaporation at a rate of 0.1 Å/sec to 0.5 Å/sec under an atmospheric pressure of $10^{-5}$ Pa to $10^{-4}$ Pa to form a white light emitting layer;
(5) heating the product obtained in the step (4) to a temperature between 120° C. and 230° C. within 10 s, then keeping at this temperature for 10 s to 1 min, and cooling to a temperature between 20° C. and 30° C. within 3 min; and
(6) depositing an electron transport layer, an electron injection layer and a cathode layer on the white light emitting layer of the product obtained in the step (5) sequentially, to obtain the white organic light emitting diode.

* * * * *